US009393298B2

(12) United States Patent
Buchanan et al.

(10) Patent No.: US 9,393,298 B2
(45) Date of Patent: Jul. 19, 2016

(54) LIQUID STABLE BOVINE VIRUS VACCINES

(71) Applicant: Intervet Inc., Summit, NJ (US)

(72) Inventors: Sandhya Buchanan, Florham Park, NJ (US); Kevin O'Connell, Omaha, NE (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/202,194

(22) Filed: Mar. 10, 2014

(65) Prior Publication Data

US 2014/0271710 A1 Sep. 18, 2014

Related U.S. Application Data

(60) Provisional application No. 61/789,045, filed on Mar. 15, 2013.

(51) Int. Cl.
| A61K 39/215 | (2006.01) |
| A61K 39/155 | (2006.01) |
| A61K 39/12 | (2006.01) |
| A61K 39/00 | (2006.01) |

(52) U.S. Cl.
CPC .............. *A61K 39/215* (2013.01); *A61K 39/12* (2013.01); *A61K 39/155* (2013.01); *A61K 2039/5254* (2013.01); *A61K 2039/552* (2013.01); *A61K 2039/70* (2013.01); *C12N 2710/16734* (2013.01); *C12N 2760/18534* (2013.01); *C12N 2760/18634* (2013.01); *C12N 2770/20034* (2013.01); *C12N 2770/24334* (2013.01)

(58) Field of Classification Search
None
See application file for complete search history.

(56) References Cited

U.S. PATENT DOCUMENTS

| 3,155,589 | A | 11/1964 | Slater et al. |
| 4,337,242 | A | 6/1982 | Markus et al. |
| 4,451,569 | A | 5/1984 | Kobayashi et al. |
| 5,443,959 | A | 8/1995 | Kikuchi et al. |
| 5,565,318 | A | 10/1996 | Walker et al. |
| 5,593,824 | A | 1/1997 | Tremi et al. |
| 5,763,409 | A | 6/1998 | Bayol et al. |
| 5,932,223 | A | 8/1999 | Burke et al. |
| 6,039,958 | A | 3/2000 | Koyama et al. |
| 6,231,860 | B1 | 5/2001 | Fanget et al. |
| 6,331,303 | B1 | 12/2001 | Briggs et al. |
| 6,931,888 | B2 | 8/2005 | Shekunov et al. |
| 7,073,349 | B2 | 7/2006 | Shekunov et al. |
| 7,351,416 | B2 | 4/2008 | Briggs et al. |
| 7,959,929 | B2 | 6/2011 | Crawford et al. |
| 8,192,747 | B2 | 6/2012 | Vande Velde |
| 8,980,610 | B2 | 3/2015 | Selvitelli et al. |
| 2004/0038878 | A1 | 2/2004 | Tanikawa et al. |
| 2004/0154317 | A1 | 8/2004 | Shekunov et al. |
| 2005/0178020 | A1 | 8/2005 | Shekunov et al. |
| 2007/0148765 | A1 | 6/2007 | Evans et al. |
| 2007/0161085 | A1 | 7/2007 | Trager et al. |
| 2007/0190163 | A1 | 8/2007 | Malaknov et al. |
| 2007/0259348 | A1 | 11/2007 | Phadke et al. |
| 2008/0248551 | A1 | 10/2008 | Stinchcomb et al. |
| 2009/0010955 | A1 | 1/2009 | Kapil et al. |
| 2009/0274734 | A1 | 11/2009 | Daamen et al. |
| 2010/0015180 | A1 | 1/2010 | Francon et al. |
| 2010/0124557 | A1 | 5/2010 | Oberreither et al. |
| 2010/0196420 | A1 | 8/2010 | Kapil |
| 2010/0297231 | A1 | 11/2010 | Vehring et al. |
| 2011/0081380 | A1 | 4/2011 | Francon et al. |
| 2012/0213810 | A1 | 8/2012 | Burgard et al. |
| 2014/0056942 | A1* | 2/2014 | Qiao et al. ................. 424/213.1 |

FOREIGN PATENT DOCUMENTS

| EP | 0028563 A1 | 5/1981 |
| EP | 0650734 | 10/1993 |
| EP | 1123710 A1 | 8/2001 |
| GB | 1575155 | 9/1980 |
| JP | 61053227 | 3/1986 |
| WO | WO8906973 A1 | 8/1989 |
| WO | WO03087327 A2 | 10/2003 |
| WO | WO2004017990 A1 | 3/2004 |
| WO | WO2007035455 A2 | 3/2007 |
| WO | WO2010125084 A1 | 11/2010 |
| WO | WO2010125087 A1 | 11/2010 |
| WO | WO2009092703 A1 | 6/2011 |
| WO | WO2011072218 | 6/2011 |
| WO | WO2014009328 A1 | 1/2014 |
| WO | WO2014029702 A1 | 2/2014 |
| WO | WO2014140239 A1 | 9/2014 |
| WO | WO2015044337 A2 | 4/2015 |
| WO | WO2015121463 A2 | 8/2015 |
| WO | WO2015124594 A1 | 8/2015 |

OTHER PUBLICATIONS

Arakawa, et al., "Biotechnology applications of amino acids in protein purification and formulations", Amino Acids, 2007, pp. 587-605, vol. 33.

Ausar, et al., "Analysis of the Thermal and pH Stability of Human Respiratory Syncytial Virus", Molecular Pharmaceutics, 2005, pp. 491-499, vol. 2(6).

Ausar, et al., "High-throughput Screening of Stabilizers for Respiratory Syncytial Virus", Human Vaccines, 2007, pp. 68-77, vol. 3(3).

Brandau, et al., "Thermal Stability of Vaccines", Journal of Pharmaceutical Sciences, 2003, pp. 218-231, vol. 92(2).

Chen, et al., "Opportunities and challenges of developing thermostable vaccines", Expert Reviews, 2009, pp. 547-557, vol. 8(5).

Kamerzell, et al., "Protein-excipient interactions: Mechanisms and biophysical characterization applied to protein formulation development", Advanced Drug Delivery Reviews, 2011, 1118-1159, 63.

Patel, et al., "Stability Consideration for Biopharmaceuticals, Part 1", BioProcess Technical, 2011, 10 pages.

Burke, Carl J., Formulation, Stability, and Delivery of Live Attenuated Vaccines for Human Use, Critical Reviews in Therapeutic Drug Carrier Systems, 1999, 1-83, 16(1).

Cavanagh, et al., Coronavirus avian infectious bronchitis virus, Veterinary Research, 2007, pp. 281-297.

(Continued)

*Primary Examiner* — Nicole Kinsey White

(57) ABSTRACT

The present invention discloses liquid stable bovine vaccines that comprise a live attenuated virus, in sucrose, arginine, and methionine. The present invention also discloses the manufacture of such vaccines and methods of protecting an animal by administration of such vaccines.

22 Claims, No Drawings

(56) References Cited

OTHER PUBLICATIONS

Chokephaibulkit et al., Challenges for the formulation of a universal vaccine against dengue, Experimental Biology and Medicine, 2013, pp. 566-578, 238.

Crawford, et al., Transmission of Equine Influenca Virus to Dogs, Science, 2005, 482-485, 310, US.

Derwent; English Abstract of JP61053227; Title: Mixed live vaccine for Japanese encephalitis and swine parvovirus infection; Sasaki; Mar. 17, 1986.

Ellingson, et al., Vaccine efficacy of porcine reproductive and respiratory Syndrome Virus Chimeras, Vaccine, 2010, pp. 2679-2686, 28.

Garry L. Morefield, A Rational, Systematic Approach for the Development of Vaccine Formulations, The AAPS Journal, 2011, pp. 191-200, 13-2.

Mochizuki, Masami, Growth characteristics of canine pathogenic viruses in MDCK cells cultured in RPMI 1640 medium without animal protein, Vaccine, 2006, pp. 1744-1748, 24.

Medi et al., Excipient selection in biologics and vaccines formulation development, European Pharmaceutical Review, 2014, pp. 16-20, 19-1.

Papatsiros, Porcine Respiratory and Reproduction Syndrome Virus Vaccinology: A Review for Commercial Vaccines, American Journal of Animal and Veterinary Sciens, 2012, pp. 149-158, 7-4.

Saif, Linda, Bovine Respiratory Coronavirus, Veterinary Clinics of North America: Food Animal Practice, 2010, pp. 349-364, 26(2), US.

Schlehuber, et al., Towards Ambient Temperature-stable vaccines: The identification of thermally stabilizing liquid formulations for measles virus using an innovative high-throughput infectivity assay, Vaccine, 2011, pp. 5031-5039, 29.

Taguchi, et al., Antibody titers for canine parvovirus type-2, canine distemper virus, and canine adenovirus type-1 in adult household dogs, Canine Veterinary Journal, 2011, 983-986, 52.

\* cited by examiner

LIQUID STABLE BOVINE VIRUS VACCINES

CROSS-REFERENCE TO RELATED APPLICATIONS

This application claims priority under 35 U.S.C. §119(e) of provisional application U.S. Ser. No. 61/789,045 filed Mar. 15, 2013, the contents of which are hereby incorporated by reference in their entireties.

FIELD OF THE INVENTION

The present invention pertains to liquid stable bovine vaccines that comprise a live attenuated bovine virus. The invention also pertains to the manufacture of such vaccines and methods of vaccinating animal subjects.

BACKGROUND

There are a significant number of viruses that can infect cattle. Such viruses include bovine viral diarrhea virus types 1 and 2, (BVDV1 and BVDV2), infectious bovine rhinotracheitis (IBR) virus, parainfluenza type 3 (PI3), bovine respiratory syncytial virus (BRSV), and bovine respiratory coronavirus (BRCV). In addition, there are a number of bacteria that can infect cattle too, including *Pasteurella multocida, Mannheimia haemolytica, Histophilus somni*, and *Mycoplasma bovis.*

It is now widely accepted that the best way of preventing disease due to bacterial or virus infections in bovine is to vaccinate them against these viruses. Moreover, multivalent live attenuated virus or bacterial vaccines can be safely administered that limit the number of vaccine injections required. Accordingly, there are commercially available multivalent live virus vaccines that protect against BVDV1 and BVDV2, IBR, PI3, and/or BRSV. However, heretofore, attenuated cattle viruses have been unstable when stored in liquid solutions. Therefore, most live attenuated bovine virus vaccines are lyophilized, i.e., freeze-dried, prior to their long-term storage. The live attenuated bovine virus is commonly mixed as a suspension in water with a protective agent, frozen, and then dehydrated by sublimation and secondary drying during the lyophilization process. The low temperatures of freezing and drying by sublimation, together with the low surface to volume ratios involved, can require long drying periods and thereby, significantly increase manufacturing time and costs.

In addition, there are inherent inconsistencies in large commercial drying processes due to: the inability to adjust the shelf temperature across the entire product load, variable freezing rates across the dryer, edge effects, and radiant energy effects. Increasing the drying temperature to reduce drying times is often not an option since the drying temperature has to remain significantly below the glass-transition temperature of the protective protein matrix. Moreover, the long inconsistent drying times and/or high drying temperatures often lead to structural damage to the live attenuated viruses, along with a significant loss of their biologic activity.

Consequently, in order to account for the inherent loss in efficacy, lyophilized bovine vaccines that comprise live attenuated viruses are stored with augmented titers. However, such increased titers can lead to significant adverse events should the lyophilization process actually lead to less loss of activity than anticipated. Therefore, great care is required to formulate a vaccine to contain a virus titer that is not only safely below the amount that leads to adverse events, but that also maintains sufficient efficacy in view of the virus titer loss due to lyophilisation and subsequent storage.

Furthermore, there is a limitation to the size of a lyophilisation vials and/or number of doses contained within such vials due to relatively small standard stopper sizes for the tops of these vials. Therefore, large volumes of liquid become difficult to sublimate through the relatively small openings. In addition, a large vial requires that the user to somehow transfer a large volume of diluent to the lyophilized cake in a sterile manner, whereas the rehydration of many more smaller vials is just inconvenient. Indeed, either alternative is particularly vexing in a feedlot environment where the vaccine recipients, e.g., the cattle, reside. Therefore, there is a need for new live attenuated bovine virus vaccines that can reliably retain their virus titers at a safe and efficacious level.

The citation of any reference herein should not be construed as an admission that such reference is available as “prior art” to the instant application.

SUMMARY OF THE INVENTION

In order to overcome the deficiencies of current vaccines, the present invention provides novel liquid stable, live, attenuated bovine virus vaccines, as well as their corresponding immunogenic compositions. The present invention also provides methods of administering such vaccines to an animal. The present invention further provides methods of preventing a disease in an animal through administering a vaccine of the present invention.

Accordingly, the present invention provides liquid stable vaccines that comprise a live attenuated bovine virus. In particular embodiments, the vaccine comprises sucrose, methionine, and/or an additional amino acid. In certain embodiments the additional amino acid is arginine, glycine, or glutamic acid. In certain embodiments the vaccine comprises 20 to 40% sucrose. In particular embodiments, the vaccine comprises 25 to 35% sucrose. In particular embodiments, the vaccine comprises 30 to 40% sucrose. In related embodiments the vaccine comprises 30 to 35% sucrose. In other embodiments, the vaccine comprises 28 to 32% sucrose. In more particular embodiments, the vaccine comprises 30% sucrose.

The liquid stable vaccines of the present invention can range in pH from pH 6.0 to pH 8.0. In certain embodiments the pH range is from pH 6.5 to pH 7.8. In particular embodiments the pH range is from pH 6.8 to pH 7.5. In more particular embodiments the pH range is from pH 7.0 to pH 7.4. In an even more particular embodiment the pH is 7.2.

The liquid stable vaccines of the present invention can comprise a buffer. In a particular embodiment of this type, the buffer comprises 2.5 to 50 mM phosphate, e.g., potassium phosphate (KPHOS). In a related embodiment, the buffer comprises 5 to 25 mM KPHOS. In particular embodiments, the buffer comprises 10 to 20 mM KPHOS.

In yet other embodiments the buffer can comprise 0.15 to 0.75 M arginine. In particular embodiments the buffer comprises 2.5 to 50 mM KPHOS and 0.15 to 0.75 M arginine. In more particular embodiments the buffer comprises 5 to 25 mM KPHOS and 0.15 to 0.75 M arginine. In still more particular embodiments the buffer comprises 10 to 20 mM KPHOS and 0.3 to 0.5 M arginine. In other embodiments the buffer comprises 2.5 to 50 mM phosphate. In a related embodiment, the buffer comprises 5 to 25 mM Tris. In particular embodiments, the buffer comprises 10 to 20 mM Tris. In related embodiments the Tris buffer comprises histidine, The liquid stable bovine vaccines of the present invention comprises an amino acid in addition to methionine. In certain embodiments as detailed above, the amino acid is arginine. In other embodiments, the amino acid is glycine. In yet other embodiments, the amino acid is glutamic acid. In other embodiments, the liquid stable vaccines comprise both arginine and glycine. In other embodiments, the liquid stable vaccines comprise both glutamic acid and glycine. In yet other embodiments, the liquid stable vaccines comprise both glutamic acid and arginine. In other embodiments, the liquid stable vaccines comprise arginine, glutamic acid, and glycine.

In certain embodiments the final concentration of arginine, or glutamic acid, or glycine in the liquid stable vaccine is 0.15 to 0.75 M. In related embodiments, the final concentration of arginine, or glutamic acid, or glycine in the liquid stable vaccine is 0.25 to 0.75 M. In more particular embodiments, the final concentration of arginine, or glutamic acid, or glycine in the liquid stable vaccine is 0.2 to 0.6 M. In more particular embodiments, the final concentration of arginine, or glutamic acid, or glycine in the liquid stable vaccine is 0.2 to 0.5 M. In still other embodiments, the final concentration of arginine, or glutamic acid, or glycine in the liquid stable vaccine is 0.25 to 0.45 M. In even more particular embodiments, the final concentration of arginine, or glutamic acid, or glycine in the liquid stable vaccine is about 0.45 M. In other particular embodiments, the final concentration of arginine, or glutamic acid, or glycine in the liquid stable vaccine is about 0.3 M.

In particular embodiments the final combined concentration of arginine together with glutamic acid and/or glycine in the liquid stable vaccine is 0.15 to 0.75 M. In related embodiments, the final concentration of arginine together with glutamic acid and/or glycine in the liquid stable vaccine is 0.25 to 0.75 M. In other embodiments, the final combined concentration of arginine together with glutamic acid and/or glycine in the liquid stable vaccine is 0.2 to 0.6 M. In more particular embodiments, the final combined concentration of arginine together with glutamic acid and/or glycine in the liquid stable vaccine is 0.3 to 0.5 M. In still other embodiments, the final concentration of arginine and glutamic acid, or glycine in the liquid stable vaccine is 0.25 to 0.45 M.

In even more particular embodiments, the final combined concentration of arginine together with glutamic acid and/or glycine in the liquid stable vaccine is about 0.45 M. In other particular embodiments, the final concentration of arginine together with glutamic acid and/or glycine in the liquid stable vaccine is about 0.3 M.

In particular embodiments the final concentration of methionine in the liquid stable vaccine is 1 to 100 mM. In related embodiments, the final concentration of methionine in the liquid stable vaccine is 2.5 to 25 mM. In more particular embodiments, the final concentration of methionine in the liquid stable vaccine is 5 to 10 mM. In even more particular embodiments, the final concentration of methionine in the liquid stable vaccine is about 7 mM.

In other particular embodiments the final concentration of methionine in the liquid stable vaccine is 0.025 to 0.3 M. In related embodiments, the final concentration of methionine in the liquid stable vaccine is 0.04 to 0.15 M. In more particular embodiments, the final concentration of methionine in the liquid stable vaccine is 0.06 to 0.09 M. In even more particular embodiments, the final concentration of methionine in the liquid stable vaccine is about 0.07 M.

In addition, the liquid stable vaccines of the present invention can also further comprise a chelating agent. In particular embodiments the chelating agent is ethylenediaminetetraacetic acid (EDTA). In certain embodiments of this type the liquid stable vaccine comprises 0.050 to 1 mM EDTA. In particular embodiments the liquid stable vaccine comprises 0.25 to 0.75 mM EDTA. In more particular embodiments the liquid stable vaccine comprises about 0.5 mM EDTA.

In certain embodiments the liquid stable vaccines of the present invention can further comprise one or more free radical scavengers and/or an antioxidants as a component. In a particular embodiment of this type a vaccine of the present invention comprises ascorbic acid. In a particular embodiment of this type the liquid stable vaccine comprises about 0.5 mM ascorbic acid. In a related embodiment the vaccine comprises alpha-tocopherol. In a particular embodiment of this type the liquid stable vaccine comprises about 0.5 mM alpha-tocopherol. In yet another embodiment, the vaccine comprises glutathione. In a particular embodiment of this type the liquid stable vaccine comprises about 3 mM glutathione. In still another embodiment, the vaccine comprises both alpha-tocopherol and ascorbic acid. In yet another embodiment the vaccine comprises both alpha-tocopherol and glutathione. In still another embodiment, the vaccine comprises both glutathione and ascorbic acid. In yet another embodiment the vaccine comprises ascorbic acid, alpha-tocopherol, and glutathione, In particular embodiments the liquid stable vaccines of the present invention can further comprise a detergent and/or surfactant. In a certain embodiments of this type the surfactant is a polyoxyethylene-polyoxypropylene block copolymer. In a particular embodiment of this type the liquid stable vaccine comprises about 0.01% polyoxyethylene-polyoxypropylene block copolymer. In a specific embodiment of this type the polyoxyethylene-polyoxypropylene block copolymer is PLURONIC®F-68. In related embodiments, the liquid stable vaccines of the present invention are maintained in sealed containers that have an inert gas such as argon, nitrogen, or helium, above the liquid (e.g., have been back-filled with the inert gas). The liquid stable vaccines of the present invention can also comprise an adjuvant.

The liquid stable vaccines of the present invention can comprise a live attenuated bovine virus. In certain embodiments the live attenuated bovine virus is infectious bovine rhinotracheitis (IBR) virus. In other embodiments the live attenuated bovine virus is parainfluenza type 3 (PI3) virus. In yet other embodiments the live attenuated bovine virus is bovine respiratory syncytial virus (BRSV). In still other embodiments the live attenuated bovine virus is bovine respiratory coronavirus (BRCV). In yet other embodiments the live attenuated bovine virus is bovine viral diarrhea type 1 virus (BVDV1). In still embodiments the live attenuated bovine virus is bovine viral diarrhea type 2 virus (BVDV2).

In addition, the present invention provides liquid stable vaccines that are multivalent vaccines. The multivalent vaccines of the present invention can contain any combination of bovine viruses. In certain embodiments the multivalent vaccines of the present invention comprise both killed bovine viruses and live attenuated bovine viruses. In a particular embodiment of this type, the multivalent vaccine comprises killed BVDV1, killed BVDV2, and killed IBR, together with live attenuated PI3 and live attenuated BRSV. In a related embodiment, the multivalent vaccine comprises killed BVDV1, killed BVDV2, and killed IBR, together with live attenuated PI3, live attenuated BRSV, and live attenuated BRCV.

In other embodiments the multivalent vaccines of the present invention comprise only live attenuated bovine viruses. In particular embodiments, the multivalent vaccine comprises live attenuated IBR and live attenuated PI3. In other embodiments, the multivalent vaccine comprises live attenuated IBR and live attenuated BRSV. In yet other embodiments, the multivalent vaccine comprises live attenuated IBR and live attenuated BRCV. In yet other embodiments, the multivalent vaccine comprises live attenuated PI3 and live attenuated BRSV. In still other embodiments, the multivalent vaccine comprises live attenuated PI3 and live attenuated BRCV. In yet other embodiments, the multivalent vaccine comprises live attenuated BRSV and live attenuated BRCV. In still other embodiments, the multivalent vaccine comprises live attenuated BVDV1 and live attenuated BVDV2. In other embodiments, the multivalent vaccine comprises live attenuated BVDV1 and IBR. In still other embodiments, the multivalent vaccine comprises live attenuated BVDV1 and PI3. In yet other embodiments, the multivalent vaccine comprises live attenuated BVDV1 and live attenuated BRSV. In still other embodiments, the multivalent vaccine comprises live attenuated BVDV1 and live attenuated BRCV. In other embodiments, the multivalent vaccine comprises live attenuated BVDV2 and live attenuated IBR. In still other embodiments, the multivalent vaccine comprises live attenuated BVDV2 and live attenuated PI3. In yet other embodiments, the multivalent vaccine comprises live attenuated BVDV2 and live attenuated BRSV. In still other embodiments, the multivalent vaccine comprises live attenuated BVDV2 and live attenuated BRCV.

In related embodiments, the multivalent vaccine comprises live attenuated IBR, live attenuated PI3, and live attenuated BRSV. In yet other embodiments, the multivalent vaccine comprises live attenuated IBR, live attenuated PI3, and live attenuated BRCV. In still other embodiments, the multivalent vaccine comprises live attenuated IBR, live attenuated BRSV, and live attenuated BRCV. In still other embodiments, the multivalent vaccine comprises live attenuated PI3, live attenuated BRSV, and live attenuated BRCV.

In yet other embodiments, the multivalent vaccine comprises live attenuated BVDV1, live attenuated BVDV2, and live attenuated IBR virus. In still other embodiments the multivalent vaccine comprises live attenuated BVDV1, live attenuated BVDV2, and live attenuated PI3 virus. In yet other embodiments the multivalent vaccine comprises live attenuated BVDV1, live attenuated BVDV2, and live attenuated BRSV. In still other embodiments the multivalent vaccine comprises live attenuated BVDV1, live attenuated BVDV2, and live attenuated BRCV. In other embodiments the multivalent vaccine comprises live attenuated BVDV1, live attenuated IBR virus and live attenuated PI3 virus. In yet other embodiments the multivalent vaccine comprises live attenuated BVDV1, live attenuated IBR virus, and live attenuated BRSV. In still other embodiments the multivalent vaccine comprises live attenuated BVDV1, live attenuated IBR virus, and live attenuated BRCV. In still other embodiments the multivalent vaccine comprises live attenuated BVDV2, live attenuated IBR virus and live attenuated PI3 virus. In yet other embodiments the multivalent vaccine comprises live attenuated BVDV2, live attenuated IBR virus, and live attenuated BRSV. In still other embodiments the multivalent vaccine comprises live attenuated BVDV2, live attenuated IBR virus, and live attenuated BRCV. In yet other embodiments the multivalent vaccine comprises live attenuated BVDV1, live attenuated PI3 virus, and live attenuated BRSV.

In still other embodiments the multivalent vaccine comprises live attenuated BVDV1, live attenuated PI3 virus, and live attenuated BRCV. In yet other embodiments the multivalent vaccine comprises live attenuated BVDV2, live attenuated PI3 virus, and live attenuated BRSV. In still other embodiments the multivalent vaccine comprises live attenuated BVDV2, live attenuated PI3 virus, and live attenuated BRCV. In yet other embodiments the multivalent vaccine comprises live attenuated BVDV1, live attenuated BRSV, and live attenuated BRCV. In still other embodiments the multivalent vaccine comprises live attenuated BVDV2, live attenuated BRSV, and live attenuated BRCV.

In other embodiments the multivalent vaccine comprises live attenuated IBR, live attenuated PI3 virus, live attenuated BRSV, and live attenuated BRCV. In still other embodiments the multivalent vaccine comprises live attenuated BVDV1, live attenuated BVDV2, live attenuated IBR virus, and live attenuated PI3 virus. In yet other embodiments the multivalent vaccine comprises live attenuated BVDV1, live attenuated BVDV2, live attenuated IBR virus, and live attenuated BRSV. In still other embodiments the multivalent vaccine comprises live attenuated BVDV1, live attenuated BVDV2, live attenuated IBR virus, and live attenuated BRCV. In yet other embodiments the multivalent vaccine comprises live attenuated BVDV1, live attenuated BVDV2, live attenuated PI3 virus, and live attenuated BRSV. In still other embodiments the multivalent vaccine comprises live attenuated BVDV1, live attenuated BVDV2, live attenuated PI3 virus, and live attenuated BRCV. In yet other embodiments the multivalent vaccine comprises live attenuated BVDV1, live attenuated BVDV2, live attenuated BRCV, and live attenuated BRCV.

In yet other embodiments the multivalent vaccine comprises live attenuated BVDV1, live attenuated IBR virus, live attenuated PI3 virus, and live attenuated BRSV. In still other embodiments the multivalent vaccine comprises BVDV1, live attenuated IBR virus, live attenuated PI3 virus, and live attenuated BRCV. In yet other embodiments the multivalent vaccine comprises BVDV1, live attenuated PI3 virus, live attenuated BRSV, and live attenuated BRCV. In still other embodiments the multivalent vaccine comprises live attenuated BVDV2, live attenuated IBR virus, live attenuated PI3 virus, and live attenuated BRSV. In still other embodiments the multivalent vaccine comprises BVDV2, live attenuated IBR virus, live attenuated PI3 virus, and live attenuated BRCV. In yet other embodiments the multivalent vaccine comprises BVDV2, live attenuated PI3 virus, live attenuated BRSV, and live attenuated BRCV.

In yet other embodiments the multivalent vaccine comprises live attenuated BVDV1, live attenuated BVDV2, live attenuated IBR virus, live attenuated PI3 virus, and live attenuated BRSV. In still other embodiments the multivalent vaccine comprises live attenuated BVDV1, live attenuated BVDV2, live attenuated IBR virus, live attenuated PI3 virus, and live attenuated BRCV. In yet other embodiments the multivalent vaccine comprises live attenuated BVDV1, live attenuated BVDV2, live attenuated IBR virus, live attenuated BRSV, and live attenuated BRCV. In still other embodiments the multivalent vaccine comprises live attenuated BVDV1, live attenuated BVDV2, live attenuated PI3 virus, live attenuated BRSV, and live attenuated BRCV. In yet other embodiments the multivalent vaccine comprises live attenuated BVDV1, live attenuated IBR virus, live attenuated PI3 virus, live attenuated BRSV, and live attenuated BRCV. In still other embodiments the multivalent vaccine comprises live attenuated BVDV2, live attenuated IBR virus, live attenuated PI3 virus, live attenuated BRSV, and live attenuated BRCV. In particular embodiments of this type, the multivalent vaccine comprises live attenuated BVDV1, live attenuated BVDV2, live attenuated PI3 virus, live attenuated IBR virus, live attenuated BRSV, and live attenuated BRCV.

The present invention further provides methods of aiding in the protection of a bovine against a clinical disease that arises from a bovine virus infection comprising administering a vaccine of the present invention to the animal. Accordingly, the present invention provides methods that comprise administering to a bovine any liquid stable vaccine of the present invention. In certain embodiments the administration is performed mucosally. In other embodiments the administration is performed parenterally. In still other embodiments the administration is performed intradermally. In yet other embodiments the administration is performed transdermally. In more specific embodiments, a vaccine of the present invention is administered to the animal subcutaneously. In other specific embodiments, a vaccine of the present invention is administered to the animal intramuscularly. The present invention also includes the use of primary and/or booster vaccines.

Any of the liquid stable vaccine of the present invention also can be combined with one or more attenuated or killed bacterial antigens such as *Pasteurella multocida, Mannheimia haemolytica, Histophilus somni*, and *Mycoplasma bovis* prior to administration. In a specific embodiment the liquid stable vaccine comprises a live attenuated IBR virus with a live attenuated or killed *Pasteurella multocida*, a live attenuated or killed *Mannheimia haemolytica* (plus or minus a live attenuated or killed *Histophilus somni*). In other embodiments the liquid stable vaccine comprises a live attenuated PI3 virus and a live attenuated BRSV with a live attenuated or killed *Pasteurella multocida*, a live attenuated or killed *Mannheimia haemolytica* (plus or minus a live attenuated *Histophilus somni*). In still other embodiments, the liquid stable vaccine comprises a live attenuated PI3 virus, a live attenuated IBR virus, and a live attenuated BRSV with a live attenuated or killed *Pasteurella multocida*, a live attenuated or killed *Mannheimia haemolytica* (plus or minus a live attenuated *Histophilus somni*). In yet other embodiments, the liquid stable vaccine comprises a live attenuated PI3 virus, a live attenuated IBR virus, a live attenuated BRSV, and a live attenuated BRCV with a live attenuated or killed *Pasteurella multocida*, a live attenuated or killed *Mannheimia haemolytica* (plus or minus a live attenuated *Histophilus somni*). In another such embodiment is the liquid stable vaccine that comprises a live attenuated PI3 virus, a live attenuated BRSV, a live attenuated BRCV is combined with a live attenuated *Pasteurella multocida*, a live attenuated *Mannheimia haemolytica* (plus or minus a live attenuated *Histophilus somni*).

Methods of making any and all of the liquid stable bovine vaccines of the present invention are also provided. In certain embodiments the method comprises combining a therapeutically effective amount of a live attenuated virus with a 20-40% sucrose, methionine and an additional amino acid and a buffered solution at pH 6.0 to pH 8.0 to form a liquid stable vaccine. The additional amino acid can be arginine, glycine, glutamic acid, or combinations of arginine, glycine, and/or glutamic acid. In particular embodiments the arginine and/or glycine and/or glutamic acid has a final concentration of 0.15 to 0.75 M in the liquid stable vaccine. In certain embodiments the methionine has a final concentration of 0.025 to 0.3 M in the liquid stable vaccine. In particular embodiments the therapeutically effective amount of a live attenuated virus is a therapeutically effective amount of a live attenuated bovine virus. In specific embodiments of this type, the therapeutically effective amount of a live attenuated bovine virus includes therapeutically effective amounts of live attenuated PI3 virus, live attenuated IBR virus and live attenuated BRSV. In a more particular embodiment of this type, the therapeutically effective amount of a live attenuated bovine virus includes therapeutically effective amounts of live attenuated PI3 virus, live attenuated IBR virus, live attenuated BRSV, and live attenuated BRCV.

These and other aspects of the present invention will be better appreciated by reference to the following Detailed Description.

DETAILED DESCRIPTION OF THE INVENTION

Because the liquid stable bovine virus vaccines of the present invention comprise live attenuated viruses, heretofore particular care would have been needed during the formulation of the vaccine to maintain the titer of the attenuated viruses at a level that is safely below that which can lead to a significant adverse event. Indeed, most live attenuated bovine virus vaccines are lyophilized, and lyophilization can lead to substantial declines in the efficacy of the attenuated live virus vaccines both due to the lyophilization process itself, as well as over time during long-term storage.

The present invention has overcome this problem by providing liquid stable bovine vaccines that remain efficacious, even during storage, without needing to increase the initial titer of the live attenuated viral antigen above a reliably safe level. As an additional benefit, the present invention provides a means for lowering the cost of manufacture of the vaccines provided by significantly reducing the amount of live attenuated bovine viruses necessary to make such a safe and efficacious vaccine. In addition, the live attenuated bovine virus vaccines of the present invention are more convenient to use than their lyophilized counterparts. Accordingly, the present invention provides safe and efficacious live attenuated bovine virus vaccines that can be stored as liquids at refrigerated temperatures and still remain stable for 12 to 18 months, and/or 18 to 24 months, and/or even longer.

Moreover surprisingly, the liquid stable live virus vaccines of the present invention can include bovine viruses of any type. Thus, the liquid stable live bovine virus vaccines of the present invention can include both enveloped and non-enveloped bovine viruses. In addition, the liquid stable live virus vaccines of the present invention can include live attenuated bovine viruses having single-stranded RNA genomes, single-stranded DNA genomes, or double-stranded DNA genomes.

The use of singular terms for convenience in the description is in no way intended to be so limiting. Thus, for example, reference to a "sugar additive" includes reference to one or more of such sugar additives, unless otherwise specified. The use of plural terms is also not intended to be limiting, unless otherwise specified. Similarly, a chemical compound that can be referred to as an acid or its corresponding base, unless otherwise specified, when denoted herein as either is intended to mean either form of the compound. Thus, the use of the term glutamic acid is meant to include glutamate and vice versa.

As used herein, a "vaccine" is a composition that is suitable for application to an animal (including, in certain embodiments, humans) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least one year when stored at or below 7° C. (e.g., in a standard refrigerator, and/or at 0° C.-7° C.). In particular embodiments a liquid stable vaccine remains efficacious when stored at or below 7° C. for at least 1.5 years. In more particular embodiments a liquid stable vaccine remains efficacious when stored at or below 7° C. for at least 2 years. In still more particular embodiments a liquid stable vaccine remains efficacious when stored at or below 7° C. for at least 2.5 to 3 years.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The term "prophylactically-effective amount" refers to the amount of a composition that when administered to bovine significantly reduces the likelihood and/or extent of an infection/infestation due to a given pathogen.

"Metaphylaxis" is the timely mass medication of an entire group of animals to eliminate or minimize an expected outbreak of disease, e.g. in one or more animals at high risk of infection/infestation. In one particular embodiment, high risk calves are light weight, commingled, long haul cattle with unknown health histories.

The term "chemoprophylaxis" refers to the administration of a medication/treatment, e.g., one or more prophylactic compositions, for the purpose of preventing or reducing viral, bacterial, and/or parasitic infection/infestation; and/or preventing or reducing disease and/or symptoms related to that infection/infestation.

The term "prophylactic composition" refers to any agent used singularly or in combination with other agents that significantly reduces the likelihood and/or extent of an infection/infestation due to a given pathogen in bovine. In one such embodiment the bovine are at high risk of developing bovine respiratory disease. following commingling, transportation, changes in weather, changes in nutrition, and/or other stressors that can initiate a symptom and/or a disease related to the presence of the viral, bacterial, or parasitic pathogens commonly associated with bovine, targeted by the agent or combination of agents.

As used herein, the term "therapeutically effective amount" is an amount of a given antigen, e.g., live attenuated bovine virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein a "sugar additive" is a 5 to 12 carbon sugar (e.g., sucrose, maltose, trehalose, dextrose, lactose, glucose, fructose, galactose) or sugar alcohol/polyol (e.g., sorbitol, mannitol, arabitol, inositol, maltitol). Unless otherwise specifically stated to the contrary, the percent (%) of the sugar additive is provided as a weight (w) of the sugar additive to the volume (v) of the vaccine, (w/v) in the vaccine.

As used herein, unless otherwise specifically stated to the contrary, the percent (%) of a solid additive, e.g., sugar additive or gelatin, in a vaccine is based on a 1% solution being 1 g of solid/100 ml of vaccine volume (w/v).

As used herein, unless otherwise specifically stated to the contrary, the percent (%) of a liquid additive, e.g., ethanol, in a vaccine is based on a 1% solution being 1 ml of liquid additive/100 ml of vaccine volume (v/v).

As used herein, the term, "approximately," is used interchangeably with the term "about" and generally signifies that a value is within twenty-five percent of the indicated value, unless otherwise indicated.

As used herein, unless otherwise specifically stated to the contrary, the pH value provided is the pH value determined/measured at 25° C.

Because the liquid stable vaccines of the present invention ideally range in pH from pH 6.0 to pH 8.0, the liquid stable vaccines of the present invention can comprise a buffer. Buffers for use in the liquid stable vaccines of the present invention include but are not limited to: potassium phosphosphate, sodium phosphate, Tris, Tris-Histidine, BIS-Tris, BIS-Tris-Propane, sodium or potassium pyrophosphate, imidazole, PIPES, ACES, MOPS, MOPSO, BES, TES, tricine, glycylglycine, and HEPES. The buffers can be brought to the desired pH with the use of any suitable counterion.

Multivalent Vaccines:

The present invention provides liquid stable multivalent vaccines. A liquid stable multivalent bovine vaccine of the present invention can include two or more antigens including one or more of the following live attenuated bovine viruses: BVDV1, BVDV2, PI3 virus, IBR virus, BRSV, and/or BRCV. As noted above, a liquid stable multivalent bovine vaccine of the present invention can also include one or more of the following live attenuated viruses: BVDV1, BVDV2, PI3 virus, IBR virus, BRSV, and/or BRCV, along with one or more killed bovine viruses.

In addition, a liquid stable vaccine of the present invention can be subsequently combined with one or more live attenuated or killed bacterial vaccine comprising an antigen such as *Pasteurella multocida*, *Mannheimia haemolytica*, *Histophilus somni*, and *Mycoplasma bovis* prior to administration. Accordingly, in certain embodiments the attenuated bacterial vaccine comprises an attenuated *Mannheimia hemolytica*. In particular embodiments of this type, the attenuated *Mannheimia hemolytica* is a leukotoxin deletant. In a specific embodiment of this type, the attenuated *Mannheimia hemolytica* is an avirulent, live *Mannheimia haemolytica* in which the gene encoding leukotoxin A was modified to be missing the nucleotide sequence that encodes amino acids 34-378 of the leukotoxin A protein [see, U.S. Pat. No. 6,331,303 B1, hereby incorporated by reference in its entirety].

In yet other embodiments the attenuated bacterial vaccine comprises an attenuated *Pasteurella multocida*. In more particular embodiments the *Pasteurella multocida* comprises a deletion in its hyaE gene. In a specific embodiment of this type, the attenuated *Pasteurella multocida* is a live, avirulent, *Pasteurella multocida* in which the gene encoding the hyaE protein was modified to be missing the nucleotide sequence that encodes amino acids 239-359 of the hyaE protein, and/or missing nucleotides 718-1084 [see, U.S. Pat. No. 7,351,416 B2, hereby incorporated by reference in its entirety]. In yet other embodiments the attenuated bacterial vaccine comprises an attenuated *Histophilus somni*. In more particular embodiments the *Histophilus somni* is live, avirulent *Histophilus somni* that is an aroA mutant.

In particular embodiments of the methods of the present invention, the attenuated bacterial vaccine comprises both an attenuated *Mannheimia hemolytica* and an attenuated *Pasteurella multocida*. In a more specific embodiment, the antibacterial composition is an attenuated bacterial vaccine comprising an avirulent, live *Mannheimia haemolytica* in which the gene encoding leukotoxin A was modified to be missing the nucleotide sequence that encodes amino acids 34-378 of the leukotoxin A protein, and an avirulent, live *Pasteurella multocida* in which the gene encoding the hyaE protein was modified to be missing the nucleotide sequence that encodes amino acids 239-359 of the hyaE protein and/or missing nucleotides 718-1084. In more particular embodiments of the methods of the present invention, the attenuated bacterial vaccine comprises an attenuated *Mannheimia hemolytica*, an attenuated *Pasteurella multocida*, and an avirulent *Histophilus somni*.

Adjuvants:

As indicated above, the vaccines of the present invention can include an adjuvant. In particular embodiments, the adjuvant comprises an aluminum salt. The use of aluminum salts in conjunction with live viral vaccines has been described. In particular embodiments the aluminum salt is chosen from the group consisting of aluminum phosphate, aluminum potassium phosphate, and aluminum hydroxide. Other well-known adjuvants include hydrocarbon oils and saponins.

Vaccine Administration:

The liquid stable virus vaccines of the present invention may be administered by any conventional means, for example, by systemic administration, including by parenteral administration such as, without limitation, subcutaneous or intramuscular administration. The liquid stable virus vaccines of the present invention also may be administered by mucosal administration, such as by intranasal, oral, intratracheal, rectal, and/or ocular administration. Alternatively, the vaccines may be administered via a skin patch, in a delayed release implant, scarification, or topical administration. It is contemplated that a liquid stable virus vaccine of the present invention also may be administered via the drinking water and/or food of the recipient bovine.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

In certain embodiments of the methods of the present invention, a virus vaccine of the present invention that is suitable for mucosal administration comprises an attenuated IBR virus. In more particular embodiments the virus vaccine of the present invention that is suitable for mucosal administration comprises an attenuated IBR virus, attenuated BVD type 1 and type 2 viruses, an attenuated PI3 virus, and an attenuated BRSV.

The immunogenicity level may be determined experimentally by vaccine dose titration and challenge study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the species or breed (e.g., of a bovine), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (typical for intradermal or transdermal application) and 5.0 mL. A typical range for the administration volume is between 0.2 and 2.0 mL, and about 1.0 to 2.0 mL for intramuscular or subcutaneous administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The present invention may be better understood by reference to the following non-limiting Example, which is provided as exemplary of the invention. The following Example is presented in order to more fully illustrate embodiments of the invention. It should in no way be construed, however, as limiting the broad scope of the invention.

EXAMPLE

Example 1

Stability of Liquid Bovine Virus Vaccines

Materials and Methods

Bulking Antigen Preparation:

Two sets of each viral antigen (BVDV1, BVDV2, PI3, and IBR) were produced. One set was grown in media free of animal origin, and the other set was grown in media containing components of animal origin.

Formulation Preparation: 7 formulations, 8 L for each formulation

A. Materials:

| | Ingredients: | Volume/L |
|---|---|---|
| A. | 100% Sucrose | 300 mL |
| B. | 20% Arginine | 392 mL |
| C. | 5% Methionine | 200 mL |
| D. | 0.5M EDTA | 1 mL |
| E. | 0.5M Ascorbic Acid | 1 mL |
| F. | 1.6M aTocopherol | 0.3 mL |
| G. | 0.06M Glutathione | 50 mL |
| H. | 10% Pluronic F68 | 0.8 mL |
| I. | 1M K2HPO4 | 7.2 mL |
| J. | 0.5M KH2PO4 | 7.6 mL |

| | | | | | | | | | | |
|---|---|---|---|---|---|---|---|---|---|---|
| LSV-1: | A, | B, | C, | | | | | | I, | J |
| LSV-2: | A, | B, | C, | D, | | | | | I, | J |
| LSV-3: | A, | B, | C, | | | | | H, | I, | J |
| LSV-4: | A, | B, | C, | | E, | F, | G, | | I, | J |
| LSV-5: | A, | B, | C, | D, | E, | F, | G, | | I, | J |
| LSV-6: | A, | B, | C, | D, | E, | F, | G, | H, | I, | J |
| LSV-7: | A, | B, | C, | | | | | H, | I, | J |

B. pH Adjustment:

Bulk formulations are allowed to mix for 2-3 hours, then split: 3.5 L were allocated to 4° C. (low range) and 4.5 L to 25° C. (elevated range).

Low range: formulation was chilled to 4° C. (while mixing when possible) and the pH adjusted to 7.25. The formulation was then held overnight @4° C. and the pH was checked again the next morning to insure the pH has stabilized at 7.25. If a minor adjustment was necessary at any point the appropriate acid/base was used (K2HPO4 or KH2PO4).

Elevated range: formulation was warmed to 25° C. (while mixing when possible) and pH adjusted to 7.25. The formulation was then held overnight @ 25° C. and the pH was checked again the next morning to insure the pH had stabilized at 7.25. If a minor adjustment was necessary at any point the appropriate acid/base was used (K2HPO4 or KH2PO4). The pH drift between 15°, 25° and 37° C. is nominal, so the formulation was amped and store at each of the 3 temps.

pH meter: the pH is measured using a very sensitive pH probe and meter. The meter displays the pH to 3 significant figures to the right of the decimal. There is a separate temperature probe with meter and both must be in the solution and stable. The adjustment takes a good amount of time, the pH is critical to the experiment. This pH meter is capable of a 5 point calibration curve with 3 points being an absolute minimum.

C. Filter Sterilize and Sparge with Argon:

Once the initial pH adjustment has been made all 7 formulations were filter sterilized using a 0.2 μM filter (preferred filter matrix=PES simply due to improved filter capacity). Currently filtration is performed using vacuum, a secondary benefit of vacuum filtering is the additional de-gassing of the formulation.

After the formulation has been filter sterilized it is sparged with argon gas to increase the depletion of $O_2$ which will hopefully yield lower reactivity of the formulation over time. Once sparge is complete ensure there is an argon overlay in place prior to storage (insure as tight a seal as possible for storage).

D. The morning after the formulation is prepare the pH is confirmed/adjusted to 7.25 at the desired temperature (4 or 25° C.). If the formulation and previous procedures have been performed correctly the pH should be close to 7.25. With an overnight incubation the pH will have drifted slightly due to the completion of chemical reactions associated with the earlier pH adjustment and further de-gassing.

E. Thawing Virus:

Optimal conditions should be used in thawing the virus, usually quick thaw in a warm waterbath with frequent mixing to prevent the bulk liquid from warming. The process is complete when there is a small amount of ice left in the formulation to keep things cold until it is ready for use and to remove residual heat from the liquid portion.

F. Adding Virus to Bulk Formulations: Preparation of Vaccine Blend:

250 mL of 4° and 750 mL of 25° C. formulations are removed from bulks of each formulation (all 7 formulations) and put into an appropriate container (Nalgene screw cap bottles). When the virus is added in a very short time frame (a few minutes) then the virus may be added with no further issues. When the virus is not immediately added, an argon overlay should be put in place to displace residual $O_2$. Once the virus has been added a fresh argon overlay should be put into place prior to mixing. The argon gas should be added to the bottle using a low flowrate.

G. Filling the Vaccines:

Formulation Filling order: 4° C. formulation should always be filled before the 25° C. sister formulation.

Analytical Methods

All cell culture assays are performed in a clean cell environment. Manipulations, dilutions and media addition are done in a Class II biological safety cabinet under aseptic conditions. All plates, bottles, flasks, pipets, pipette tips and dilution tubes must be sterilized before use. All media and associated ingredients must be sterile.

BVD Type1 Potency:

A suitable cell line for growth of BVD is used for this titration assay. For example, Madin-Darby Bovine Kidney cells (MDBK) cells are grown to confluency in a flask or roller bottle using Hanks Modified Essential Media (HMEM) supplemented with 5-10% Fetal Bovine Sera (FBS), L-glutamine and an antibiotic (gentamicin (12-25 µg/mL)). The media is decanted from a flask/roller bottle of healthy growing MDBK cells approximately 24 hours before the desired time of viral titration. Rinse the serum containing media from the flask/roller bottle using Phosphate Buffered Saline, pH 7.2 (PBS). Decant and replace with a solution containing the appropriate amount of Trypsin/EDTA to gently loosen the cells from the surface of the flask/roller bottle. The amount of trypsin should be adjusted to the size of the flask or roller bottle surface. Place the flask/roller bottle containing the trypsinized cells into a 37 C incubator for enough time to allow the cells to detach. When the cells appear to be at the right level of detachment, add 5-20 mL of Eagles Modified Essential Media containing with L-glutamine and gentamicin (EMEM). 5% FBS is added to the EMEM to neutralize the trypsin. Pipet the cells to break up the clumps. Determine the cell density using a hemocytometer. The viability can be determined using a 4% solution of Trypan Blue. Dilute the cells to $1 \times 10^5$ cells per mL in EMEM with 5% FCS and add 100 µL to each well of a 96-well tissue culture plate. To prevent the media from evaporating, cover the plate and place cells in a humidified incubator set at 37 C with 5% $CO_2$. Prepare tubes to be used for the 10-fold dilutions for virus titration by adding the appropriate amount of EMEM/5% serum to each of the tubes. A separate tube is filled with EMEM for the negative control. Make the 10-fold dilutions of the virus sample into the prepared tubes. A prepared reference of Type 1 BVD with known titer is also diluted in EMEM and used as a positive control. Ensure that the 96-well plate is confluent with a healthy monolayer of MDBK cells and apply 100 µL of each of the diluted virus samples to the appropriate wells of the 96-well MDBK cell plate. Include the negative and positive controls. Replace the lid on the plate and place in a humidified 37 C, 5% CO2 incubator for approximately 4 days. After 4 days, the plates may be read using an inverted microscope and examining the plate for cytopathic effect (CPE) of the virus on the cells. If the strain of BVD is a non-cytopathic strain, the following procedure may be used to determine the virus titer. After 4 days, removed the infected plates from the incubator and decant the media into an appropriate waste container. Rinse the monolayer 2-times with PBS. After the second wash, remove the excess moisture by gently taping the plate against absorbent paper. Fix the cell substrates under a fume hood with 50-200 µL/well of cold 70% acetone/30% methanol fixative and allow the plate to fix at room temperature for 10 minutes. Decant the used fixative into an appropriate vessel. Remove excess moisture by gently tapping the plate against absorbent paper and allow the plate to air dry. The fixed plates may be stored at 2-7 C for up to 30 days before staining. To stain the plates, rinse each once with PBS and tap off the excess moisture. Add 50-75 uL per well of an antibody directed specifically towards a BVD, type 1 virus. Replace the lid on the plates and incubate humidified at 37 C in 5% CO2 for 30-60 minutes. Remove the plates from the incubator and decant the fluid containing the unattached antibody. Rinse the plate at least 2× to remove the unbound antibody. Add 50-75 µL of fluorescent isothiocyanate tagged (FITC) secondary antibody diluted to the appropriate level to each well of the plate using a multichannel pipette. Replace the cover and incubate the plates in a humidified 37 C, 5% $CO_2$ incubator for approximately 30 minutes. Remove the plates from the incubator, remove the lid and decant the unbound FITC labeled antibody. Rinse the plates with PBS twice and tap the plates on absorbent paper to remove the excess moisture. The plates may be read immediately using a fluorescent microscope with the appropriate filters for the FITC conjugate. The infected substrate will contain cells with a cytoplasm that appears apple green and nuclei that are dark (unstained). For a cytopathic strain of BVD, consider wells showing obvious CPE as positive. All negative control wells should remain negative and not show CPE or stain positive. Calculate the virus titer by the Spearman-Karber method and report as the $\log_{10} TCID_{50}/mL$. The test is valid if the negative controls are negative and the positive control falls within the expected range of titer for the sample.

BVD Type 2 Potency:

BVD type 2 potency testing is done exactly the same as that for BVD type 1. If the strain is a non-cytopathic strain, then an antibody directed against the type 2 strain should be used. The positive control virus will be BVD type 2.

IBR Potency:

A suitable cell line for growth of IBR is used for this titration assay. For example, Madin-Darby Bovine Kidney cells (MDBK) cells are grown to confluency in a flask or roller bottle using Hanks Modified Essential Media (HMEM) supplemented with 5-10% Fetal Bovine Sera (FBS), L-glutamine and an antibiotic (gentamicin (12-25 µg/mL)). The media is decanted from a flask/roller bottle of healthy growing MDBK cells approximately 24 hours before the desired time of viral titration. Rinse the serum containing media from the flask/roller bottle using Phosphate Buffered Saline, pH 7.2 (PBS). Decant and replace with a solution containing the appropriate amount of Trypsin/EDTA to gently loosen the cells from the surface of the flask/roller bottle. The amount of trypsin should be adjusted to the size of the flask or roller bottle surface. Place the flask/roller bottle containing the trypsinized cells into a 37 C incubator for enough time to allow the cells to detach (5-10 minutes). When the cells appear to be at the right level of detachment, add 5-20 mL of Eagles Modified Essential Media containing with L-glutamine and gentamicin (EMEM). 5% FBS is added to the EMEM to neutralize the trypsin. Pipet the cells to break up the clumps. Determine the cell density using a hemocytometer. The viability can be determined using a 4% solution of Trypan Blue. Dilute the cells to $2.4 \times 10^5$ cells per mL in EMEM with 5% FCS and add 5 mL to each well of a 60 mm tissue culture plates. To prevent the media from evaporating, cover the plate and place cells in a humidified incubator set at 37 C with 5% $CO_2$. Prepare tubes to be used for the 10-fold dilutions for virus titration by adding the appropriate amount of EMEM/5% serum to each of the tubes. A separate tube is filled with EMEM for the negative control. Make the 10-fold dilutions of the virus sample into the prepared tubes. A prepared reference of IBR with known titer is also diluted in EMEM and used as a positive control. Ensure that the 60 mm plates are confluent with a healthy monolayer of MDBK cells. Label each plate with the sample identification and dilutions to be plated. The media is then decanted from each of the 60 mm plates. Inoculate each of the plates with 100 µL of sample to be tested, including the negative and positive controls. Tilt plates back and forth to distribute the inoculum. Replace the lid on the plate and place in a humidified 37 C, 5% CO2 incubator for approximately 60 minutes for absorption. Following absorption of the virus, add 5 mL of overlay medium consisting of Dulbecco's Minimal Essential Medium (DMEM), with 5% FCS, L-glutamine, gentamicin and carboxymethylcellulose to each 60 mm plate. After 4 days, decant the CMC overlay medium from each plate. Rinse each plate with water and decant. Add 2 mL (or enough to cover the bottom) of Crystal Violet stain to each plate or well, and incubate at room temperature (15-30 C) for 20-30 minutes. Gently rinse the stain from each plate with cold water. Invert the plates and allow the plates to dry. After the plates have dried, visually count the plaques on the plates using an inverted microscope. Only use the dilutions that have average numbers of plaques between 10 and 150 to determine titer. Calculate the Plaque Forming Unit (PFU) virus titer/0.1 mL by the following calculation: PFU titer/0.1 mL=$Log_{10}$(average of plaques counted for each dilution of each individual titer)+$Log_{10}$(dilution factor). Report titers as $Log_{10}$ $TCID_{50}$/mL. The test is valid if the negative control shows no sign of plaques in the wells and the positive control titer is within the expected range.

BRSV Potency:

A suitable cell line for growth of BRSV is used for this titration assay. For example, Vero cells are grown in a flask or a roller bottle to confluency. The Vero cells can be grown on Dulbeccos modified essential media (DMEM), supplemented with antibiotics (gentamicin (12-50 µg/mL), fetal bovine sera (FBS 5%) and L-glutamine (2 mM). Titration plates are prepared approximately 24 hours before needed. The media is decanted from the healthy monolayer of Vero cells. The cells are rinsed with PBS. A small amount of trypsin/EDTA is added to the flask/roller bottle to loosen the cells from the surface. The flask/roller bottle is then incubated at 37 C for 5-10 minutes, at which time they are observed for detachment from the surface. Eagles modified essential media with antibiotics, L-glutamine, non-essential amino acids, lactalbumin hydrolysate (LAH 0.05%) and glucose (0.3%) is added to the flask (5-20 mL) containing trypsin/EDTA and the cells are pipetted to break up the clumps of cells. A hemocytometer is used to determine the number of cells, using a counter stain to determine the viability count for the cells. The cells are diluted to a final concentration of $1 \times 10^5$, using the EMEM as a diluent. Using a multichannel pipet, add 100 µL of the diluted cells to each well of a 96-well plate. Place the inoculated plates in a humidified incubator at 37 C, 5% $CO_2$ to allow the cells to attach and grow. Prepare tubes to be used for the 10-fold dilutions for virus titration by adding the appropriate amount of EMEM to each of the tubes. A separate tube is filled with EMEM for the negative control. Make the 10-fold dilutions of the virus sample into the prepared tubes. A prepared reference of BRSV with known titer is also diluted in EMEM and used as a positive control.

Ensure that the 96-well plate is confluent with a healthy monolayer of Vero cells and apply 100 µL of each of the diluted virus samples to the appropriate wells of the 96-well Vero cell plate. Include the negative and positive controls. Replace the lid on the plate and place in a humidified 37 C, 5% CO2 incubator for approximately 8 days before evaluation. On the eight day, an inverted microscope is used to evaluate each well of the 96-well plate for cytopathic effect (CPE). The negative control is viewed first to determine the amount of background debris that is the baseline for each well. Record the number of CPE positive wells for each dilution. Calculate the virus titer by using the Spearman-Karber method and report as $Log_{10}$ $TCID_{50}$/mL. The test is valid if the negative control shows no sign of CPE in the wells and the positive control titer is within the expected range.

PI3 Potency:

A suitable cell line for growth of PI3 is used for this titration assay. For example, Vero cells are grown in a flask or a roller bottle to confluency. The Vero cells can be grown on Dulbeccos modified essential media (DMEM), supplemented with antibiotics (gentamicin (12-50 µg/mL), fetal bovine sera (FBS 5%) and L-glutamine (2 mM). The media is decanted from the healthy monolayer of Vero cells. The cells are rinsed with PBS. A small amount of trypsin/EDTA is added to the flask/roller bottle to loosen the cells from the surface. The flask/roller bottle is then incubated at 37 C for 5-10 minutes, at which time they are observed for detachment from the surface. Eagles modified essential media with gentamicin, L-glutamine and 5% FCS is added to the flask (5-20 mL) containing trypsin/EDTA and the cells are pipetted to break up the clumps of cells. A hemocytometer is used to determine the number of cells, using a counter stain (Trypan Blue) to determine the viability count for the cells. The cells are diluted to a final concentration of $1 \times 10^5$, using the EMEM as a diluent. Using a multichannel pipet, add 100 µL of the diluted cells to each well of a 96-well plate. Place the inoculated plates in a humidified incubator at 37 C, 5% $CO_2$ to allow the cells to attach and grow. Prepare tubes to be used for the 10-fold dilutions for virus titration by adding the appropriate amount of EMEM to each of the tubes. A separate tube is filled with EMEM for the negative control. Make the 10-fold dilutions of the virus sample into the prepared tubes. A prepared reference of PI3 with known titer is also diluted in EMEM and used as a positive control. Ensure that the 96-well plate is confluent with a healthy monolayer of Vero cells and apply 100 µL of each of the diluted virus samples to the appropriate wells of the 96-well Vero cell plate. Include the negative and positive controls. Replace the lid on the plate and place in a humidified 37 C, 5% CO2 incubator for approximately 7 days before evaluation. On the seventh day, an inverted microscope is used to evaluate each well of the 96-well plate for cytopathic effect (CPE). The negative control is viewed first to determine the amount of background debris that is the baseline for each well. Record the number of CPE positive wells for each dilution. Calculate the virus titer by using the Spearman Karber method and report as $Log_{10}$ $TCID_{50}$/mL. The test is valid if the negative control shows no sign of CPE in the wells and the positive control titer is within the expected range.

BRCV Potency:

MDBK cells are grown using DMEM with L-glutamine, fetal bovine sera and antibiotics (Growth Media) in a flask or roller bottle until a confluent monolayer of health cells is achieved. Decant the flask/bottle and rinse with phosphate buffered saline (PBS). Decant the PBS and add sufficient trypsin containing solution to detach cells from the surface. Place the culture back in a 37 C incubator to give the cells time to detach. Once the cells detach from the surface, add an amount of media equivalent to 2× the amount of trypsin used is added to the cells. The cells are pipetted several times to break up the clumps of cells. A viable count is performed using a hemocytometer or other suitable method, using Trypan blue to determine the percentage of non-viable cells in the suspension. The cell suspension is then diluted with the Growth Media to $2 \times 10^5$ cells/ml. Using a multichannel pipettor, 100 µL of the cell suspension is added to each well of a 96 well tissue culture plate. The seeded plates are incubated in at 37 C, 5% $CO_2$, high humidity until a monolayer is formed at about 90-100% confluency. Samples containing live viruses are diluted 10-fold in Inoculation Media (DMEM, L-glutamine, antibiotics and Type IX trypsin). BRCV is a trypsin dependent virus and thus trypsin must be added to the inoculation media in order for the viruses to infect the cells. FBS must not be added to the dilution media for trypsin dependent viruses. When the 96 well plates are ready, decant the Growth Media and wash the plate with PBS. Remove the PBS from the 96 well plate containing the MDBK monolayer of cells and immediately apply the diluted samples of virus to the plate. A dilution series of a positive control containing a known amount of virus is also added to the plate. A negative control series containing only media is also added to the plate. Incubate the plates at 37 C, 5% $CO_2$ for five days. After 5 days, remove the plates from the incubator and observe cells, using a microscope, for the cytopathic effect of the virus (CPE). Wells showing CPE are marked as positive, wells with intact cells are considered negative. Calculate the titers of the positive control and the samples by the Spearman-Karber method and report as $TCID_{50}$/ml. The assay is valid if the negative control wells show no sign of cytopathic effect and the positive control falls within the expected range.

Results

Multiple experiments were carried out for liquid stabilization screening. An initial study was an excipient screening using a monovalent live attenuated BRSV isolate and differing levels of sucrose, trehalose, arginine, methionine, gelatin and various other excipients. 0.5-1 mL aliquots of formulations were dispensed into 2 mL glass vaccine vial, stoppered and crimp sealed. Incubations were conducted at 25, 37 and 50° C. with the majority of conclusions made using the 25° C. data. This experiment indicated an elevated level of stability using sucrose/arginine (SA) and sucrose/arginine/methionine (SAM).

A second experiment was a buffer screening where SAM was buffered using several different buffering systems at pH=7.25. Two buffers were selected for use outside of the optimal 7.25 as well, acetate buffer at pH 7.25 and pH 4.5 in addition to borate buffer at pH 7.25 and pH 8.5. Phosphate buffer at pH 7.25 showed the least titer lost after 6 days at 37° C. Incubations were performed at 37° C. to ensure an accelerated degradation curve. Vaccine formulations were dispensed 1 mL into 2 mL glass vaccine vials, stoppered, and crimp sealed prior to incubation.

A third experiment encompassed preparing a monovalent vaccine using the same live attenuated BRSV of the initial experiment, see above, and stabilizer formulations LSV-1 through LSV-6. Stabilizer formulations were prepared, then sparged using argon gas, filter sterilized using 0.2 um syringe tip filters and an argon gas overlay was applied prior to storage. On the day of fill the virus was added and mixed, the vaccine was then dispensed 1 mL in a 2.2 mL glass ampule, back-filled with argon gas, flame sealed and incubated. All formulations except LSV-6 were demonstrating acceptable stability (see Table 1A and 1B).

TABLE 1

Stabilizer Performance- Monovalent BRSV

| Stabilizer | BRSV |
|---|---|
| A. | |
| LSV-1 | 33.4 months |
| LSV-2 | 47.1 |
| LSV-3 | 31.7 |
| LSV-4 | 46.3 |
| LSV-5 | 51.2 |
| LSV-6 | 5.4 |
| B. | |
| LSV-1 | ***** |
| LSV-2 | ***** |
| LSV-3 | ***** |
| LSV-4 | ***** |
| LSV-5 | ***** |
| LSV-6 | * |

Estimated stability based on data through 108 weeks, cut off for stability is 2 logs loss.
***** = 24+ months to 2 logs loss,
**** = 19-24 Months,
*** = 13-18 Months
** = 7-12 Months,
* = 1-6 Months The fourth experiment used all five virus fractions (BVDV1, BVDV2, IBR, PI3, and BRSV) and LSV-7 was initiated in place of LSV-6 (Table 2). Stabilizer formulations were prepared, then sparged using argon gas, filter sterilized using 0.2 um PES bottle top filters and an argon gas overlay was applied prior to storage. On the day of fill the virus was added and mixed, the vaccine was then dispensed 1 mL in a 2.2 mL glass ampule, back-filled with argon gas, flame sealed and incubated. Combination samples were also filled ~10 mL into glass and plastic vaccine vials, overlayed with argon gas, stoppered and crimp sealed. It was apparent early in the fourth experiment that there were problems during the blend for both BVDV1 and BVDV2. Both virus fractions had a much lower than expected input into the vaccine based on volumes added, it was suggested that these viruses were compromised prior blend and fill. The three remaining virus fractions were within expectations following blend and fill. Each stabilizer gave each virus a different stability profile (Tables 3 and 4).

| Chemical (Stock Reagent) | Final Conc. | LSV-1 % | LSV-2 % | LSV-3 % | LSV-4 % | LSV-5 % | LSV-6 % | LSV-7 % |
|---|---|---|---|---|---|---|---|---|
| 500 mM K2HPO4 | 11 mM | 0.0072 | 0.0072 | 0.0072 | 0.0072 | 0.0072 | 0.0072 | 0.0072 |
| 250 mM KH2PO4 | 11 mM | 0.0076 | 0.0076 | 0.0076 | 0.0076 | 0.0076 | 0.0076 | 0.0076 |
| 100% Sucrose | 30% | 30 | 30 | 30 | 30 | 30 | 30 | 30 |
| 20% Arginine | 8% | 8 | 8 | 8 | 8 | 8 | 8 | 8 |
| 6% Methionine | 1% | 1 | 1 | 1 | 1 | 1 | 1 | 1 |
| 0.5M EDTA | 0.5 mM | | 0.1 | | | 0.1 | 0.1 | 0.1 |
| 10% Pluronic F-68 | 0.01% | | | 0.008 | | | 0.008 | 0.008 |
| 0.5M Ascorbic Acid | 0.5 mM | | | | 0.1 | 0.1 | 0.1 | |
| 1.6M alpha-tocopherol | 0.5 mM | | | | 0.0003 | 0.0003 | 0.0003 | |
| 0.06M Glutathione | 3 mM | | | | 0.05 | 0.05 | 0.05 | |

TABLE 2

Stabilizer Formulations

| Stock Reagent Concentration: | Final Concentration: |
|---|---|
| 100% Sucrose = 2.92M | 30% Sucrose = 0.876M |
| 20% Arginine-HCl = 0.949M | 8% Arginine-HCl = 0.380M |
| 6% Methionine = 0.0402M | 1% Methionine = 0.067M |
| 0.5M EDTA | 0.5 mM EDTA |
| 10% Pluronic F-68 | 0.01% Pluronic F-68 |
| 1.6M alpha-Tocopherol | 0.5 mM alpha-Tocopherol |
| 0.06M Glutathione | 3 mM Glutathione |

TABLE 3

Stabilizer Results (in Months)

| Stabilizer | BRSV$_1$ (mono) Strain 1 | BRSV$_2$ (combo) strain 2 | PI3$_2$ (combo) | IBR$_2$ (combo) | BVD1$_3$ (combo) | BVD2$_3$ (combo) |
|---|---|---|---|---|---|---|
| LSV-1 | 15.7 | 32.8 | 22.3 | 14.5 | 9 | 6 |
| LSV-2 | 32.7 | 21.6 | 20.4 | 13.3 | 6 | 9 |
| LSV-3 | 22.5 | 24.1 | 14.2 | 13.4 | 9 | 6 |
| LSV-4 | 15.0 | 2.8 | 19.1 | 17.4 | 6 | 6 |
| LSV-5 | 13.8 | 2.7 | 36.8 | 25.3 | 9 | 9 |
| LSV-7 | 18.0 | 21.6 | 35.0 | 23.9 | 9 | 9 |

$_1$Stability results based on 15 months @ 4° C.
$_2$Stability results using slope calculated at 18 months @ 4° C.
$_3$Numbers of months until BVD virus was no longer detectable in the assay.

TABLE 4

Relative Stability Results

| Stabilizer | BRSV (mono) Strain 1 | BRSV (combo) Strain 2 | PI3 (combo) | IBR (combo) | BVD1 (combo) | BVD2 (combo) |
|---|---|---|---|---|---|---|
| LSV-1 | *** | ***** | **** | *** | ** | * |
| LSV-2 | ***** | **** | **** | *** | * | ** |
| LSV-3 | **** | ***** | *** | *** | ** | * |
| LSV-4 | *** | * | **** | *** | * | * |
| LSV-5 | *** | * | ***** | ***** | ** | ** |
| LSV-7 | *** | **** | ***** | **** | ** | ** |

CONCLUSIONS

Using the basic formulation of 30% sucrose, 8% arginine and 1% methionine (SAM), greater than 24 months stability was obtained for the BRSV fraction. [Two different live attenuated BRSV virus strains were tested]. That same formulation also provided over 12 months stability for the PI3 and IBR fractions.

We claim:

1. A liquid stable vaccine that comprises a live attenuated bovine virus, 20-40% (w/v) sucrose, 0.15 to 0.75 M arginine, and 0.025 to 0.3 M methionine; wherein the liquid stable vaccine has a pH of 6.0 to 8.0; and wherein the live attenuated bovine virus is selected from the group consisting of infectious bovine rhinotracheitis virus (IBR), parainfluenza type 3 virus (PI3), bovine respiratory syncytial virus (BRSV), and any combination thereof.

2. The liquid stable vaccine of claim 1 that further comprises a surfactant.

3. The liquid stable vaccine of claim 2 wherein the surfactant is polyoxyethylene-polyoxypropylene block copolymer.

4. The liquid stable vaccine of claim 1 that further comprises a chelator.

5. The liquid stable vaccine of claim 4 wherein the chelator is ethylenediaminetetraacetic acid (EDTA).

6. The liquid stable vaccine of claim 1 that further comprises an antioxidant.

7. The liquid stable vaccine of claim 6 wherein the antioxidant is selected from the group consisting of ascorbic acid, alpha-tocopherol, glutathione, and any combination thereof.

8. The liquid stable vaccine of claim 1 that further comprises a buffer.

9. The liquid stable vaccine of claim 8 wherein the buffer comprises 2.5 to 50 mM potassium phosphate.

10. The liquid stable vaccine of claim 9, wherein the live attenuated bovine virus is a live attenuated IBR.

11. The liquid stable vaccine of claim 10 that further comprises a live attenuated BRSV.

12. A method of vaccinating a bovine comprising administering to the bovine the liquid stable vaccine of claim 1.

13. A method of making a liquid stable vaccine that comprises combining a therapeutically effective amount of a live attenuated bovine virus with 20-40% (w/v) sucrose, 0.15 to 0.75 M arginine, and 0.025 to 0.3 M methionine; wherein the liquid stable vaccine has a pH of 6.0 to 8.0; and wherein the live attenuated bovine virus is selected from the group consisting of infectious bovine rhinotracheitis virus (IBR), parainfluenza type 3 virus (PI3), bovine respiratory syncytial virus (BRSV), and any combination thereof.

14. A liquid stable vaccine that comprises a live attenuated infectious bovine rhinotracheitis virus (IBR), 20-40% (w/v) sucrose, 0.15 to 0.75 M arginine, and 0.025 to 0.3 M methionine; wherein the liquid stable vaccine has a pH of 6.0 to 8.0.

15. The liquid stable vaccine of claim 14 that further comprises a live attenuated bovine BRSV.

16. The liquid stable vaccine of claim 15 that further comprises a live attenuated PI3.

17. The liquid stable vaccine of claim 14 that further comprises a live attenuated PI3.

18. The liquid stable vaccine of claim 1, wherein the live attenuated bovine virus is a live attenuated PI3.

19. The liquid stable vaccine of claim 18 that further comprises a live attenuated BRSV.

20. The liquid stable vaccine of claim 1, wherein the live attenuated bovine virus is a live attenuated BRSV.

21. The liquid stable vaccine of claim 11 that further comprises a live attenuated PI3.

22. A method of vaccinating a bovine against infectious bovine rhinotracheitis (IBR) virus, parainfluenza type 3 (PI3), and bovine respiratory syncytial virus (BRSV), comprising administering to the bovine the liquid stable vaccine of claim 16.

* * * * *